(12) United States Patent
Taylor et al.

(10) Patent No.: US 10,792,179 B2
(45) Date of Patent: Oct. 6, 2020

(54) CUSTOMIZED SPINAL BRACING TO AID IN NEUROMOTOR TRAINING

(71) Applicant: TheraTogs, Inc., Telluride, CO (US)

(72) Inventors: M. Lee Taylor, Telluride, CO (US); Beverly Cusick Taylor, Telluride, CO (US); Daniel (Dan) Lee Collins, Tempe, AZ (US)

(73) Assignee: TheraTogs, Inc., Telluride, CO (US)

( * ) Notice: Subject to any disclaimer, the term of this patent is extended or adjusted under 35 U.S.C. 154(b) by 105 days.

(21) Appl. No.: 14/684,328

(22) Filed: Apr. 10, 2015

(65) Prior Publication Data

US 2015/0290017 A1    Oct. 15, 2015

Related U.S. Application Data

(60) Provisional application No. 61/978,192, filed on Apr. 10, 2014.

(51) Int. Cl.
*A61F 5/02* (2006.01)

(52) U.S. Cl.
CPC ............... *A61F 5/02* (2013.01); *A61F 5/026* (2013.01); *A61F 5/028* (2013.01)

(58) Field of Classification Search
CPC .. A61F 5/02; A61F 5/022; A61F 5/024; A61F 5/026; A61F 5/028; A61F 5/04; A61F 5/05; A61F 5/058; A61F 5/05825; A61F 13/04
USPC .......... 602/5–7, 19, 61; 2/44, 462, 463, 467; 128/875, 869, 870–871
See application file for complete search history.

(56) References Cited

U.S. PATENT DOCUMENTS

| | | | | | |
|---|---|---|---|---|---|
| 664,250 | A | * | 12/1900 | Fitzgerald | A61F 5/028 602/19 |
| 2,828,737 | A | * | 4/1958 | Hale | A61F 5/028 602/19 |
| D186,642 | S | * | 11/1959 | Hale | 602/19 |
| 3,771,513 | A | * | 11/1973 | Velazquez | A61F 5/024 602/19 |
| 4,508,110 | A | * | 4/1985 | Modglin | A61F 5/022 2/44 |

(Continued)

FOREIGN PATENT DOCUMENTS

| | | | |
|---|---|---|---|
| DE | 3522533 A1 * | 1/1987 | ............ A61F 5/024 |
| FR | 2 682 869 A * | 10/1991 | |

(Continued)

OTHER PUBLICATIONS

Translation, FR 2 682 869 A1.*

*Primary Examiner* — Anna K Kinsaul
*Assistant Examiner* — Camtu T Nguyen
(74) *Attorney, Agent, or Firm* — Macheledt Bales LLP

(57) ABSTRACT

A thermoformable spinal brace for customizable shaping to a wearer by a skilled clinician, preferably worn under the wearer's clothes and worn over and releasably attached to a subsystem of neuromotor training garments for the torso. The subsystem of garments for the torso may include upper- and lower-torso garments whether unitary or two or more pieces interconnected with flexible straps. An anterior apron assembly with strapping is included for further support, creating a unique therapeutic mammalian musculoskeletal spinal orthosis system.

15 Claims, 7 Drawing Sheets

(56) References Cited

U.S. PATENT DOCUMENTS

| | | | | |
|---|---|---|---|---|
| 5,101,811 | A | * | 4/1992 | Brunswick ............. A47C 7/425 |
| | | | | 297/112 |
| 5,240,538 | A | * | 8/1993 | Hyams .................... A41F 15/00 |
| | | | | 156/245 |
| 7,549,970 | B2 | * | 6/2009 | Tweardy ................. A61F 5/055 |
| | | | | 128/869 |
| 2003/0220594 | A1 | * | 11/2003 | Halvorson .............. A61F 5/024 |
| | | | | 602/19 |
| 2008/0021357 | A1 | * | 1/2008 | Firsov .................... A61F 5/026 |
| | | | | 602/19 |
| 2012/0245501 | A1 | * | 9/2012 | Rossi ..................... A61F 5/026 |
| | | | | 602/19 |
| 2014/0074003 | A1 | * | 3/2014 | Monden ................. A61F 5/026 |
| | | | | 602/19 |
| 2014/0155796 | A1 | * | 6/2014 | Yang ..................... A61B 90/50 |
| | | | | 602/19 |
| 2014/0221893 | A1 | * | 8/2014 | Modglin ................. A61F 5/028 |
| | | | | 602/19 |

FOREIGN PATENT DOCUMENTS

| | | | | |
|---|---|---|---|---|
| FR | 2 682 869 | A1 | * | 10/1991 |
| FR | 2 682 869 | A1 | * | 10/1991 |
| FR | 2682869 | A1 | * | 4/1993 ............. A61F 5/028 |
| GB | 2483329 | A | * | 8/2011 |
| WO | WO 2013138468 | A1 | * | 9/2013 ............... A61F 5/03 |
| WO | WO 2014188132 | A1 | * | 11/2014 ............... A61F 5/01 |

* cited by examiner

CUSTOMIZED SPINAL BRACING TO AID IN NEUROMOTOR TRAINING

CROSS REFERENCE TO RELATED APPLICATION(S)

This application claims benefit under 35 U.S.C. 119(e) of pending U.S. Provisional Application No. 61/978,192 filed 10 Apr. 2014 by the applicant and named inventors hereof, the complete disclosure of which—including examples and sketches—is incorporated herein by reference, to the extent the disclosure of the co-pending U.S. provisional application provides support and edification of this technical disclosure.

FIELD OF THE INVENTION

In general, the invention relates to therapeutic mammalian musculoskeletal support bracing, including customizable spinal bracing worn to aid in sensorimotor or neuromotor training of a mammalian patient (human, farm livestock, an animal raised as a pet, and such); spinal bracing, as shown and described throughout, is worn to (1) provide support for weak or damaged musculoskeletal systems, (2) restrict undesirable movement, and/or (3) promote corrective movement. Conventional, currently-available musculoskeletal support bracing falls far short of the wearable low-profile uniquely multifaceted bracing solution disclosed and contemplated herein.

More particularly, the invention is directed to a unique thermoformable spinal brace for customizable shaping to an individual wearer by a skilled clinician, preferably worn under the wearer's clothes and worn over and attached to a subsystem of upper- and lower-torso neuromotor training garments and straps, the combination of which is arranged in a configuration determined to accommodate one or more of the following: to aid in improved spinal alignment; to aid in improved posture; to aid in increased and improved respiration; to restrict gross trunk motion in the sagittal plane; to produce intracavitary pressure in the trunk and thereby reduce load on the intervertebral discs; and/or to improve the quality of movement of the wearer—whether by inhibiting or restricting undesirable movement or encouraging corrective movement, lending postural or structural support, and so on, to meet therapeutic or treatment objectives. The thermoformable spinal brace can be fabricated from one or more layers, such as a laminate, including a layer comprising a low-temperature thermoplastic material.

GENERAL BACKGROUND OF THE INVENTION

By way of general technical background in connection with the instant technical disclosure, background information is offered including two U.S. patents issued to the assignee of the instant invention, the inventor of which is a co-inventor hereof, illustrating therapeutic garment systems to which the instant spinal brace structure of the invention is releasably securable as contemplated herein: U.S. Pat. No. 8,007,457 issued to Beverly Cusick Taylor on 30 Aug. 2011 and U.S. Pat. No. 8,535,256 issued to Beverly Cusick Taylor on 17 Sep. 2013. Both disclosures of these patents are incorporated herein by reference for their detailed description and rigorous technical analysis and discussion of the underlying garment subsystems suitable for use with the spinal brace and anterior apron assembly to facilitate achievement of one or more therapeutic objective. ATTACHMENT A is hereby fully incorporated by reference herein; it is drawing sheet 5 of 5 of the inventors' pending U.S. Prov. App. No. 61/978,192 depicting a sample/selection of figures labeled PRIOR ART from U.S. Pat. No. 8,007,457 (namely, FIGS. 18A,B, 34, 38, 40, 41) highlighting unique features of an upper-torso component 20 and lower-torso component 30 suitable for use according to the invention to which a brace structure 10, 100, 400, 410 can be releasably secured. ATTACHMENTS B and C are hereby incorporated by reference herein: each depict underlying garment subsystem products designed by at least one co-inventor hereof and offered by the applicant-assignee of the instant invention.

SUMMARY OF THE INVENTION

One will appreciate the distinguishable features of the new therapeutic mammalian musculoskeletal spinal orthosis system composed of a support bracing structure, anterior apron assembly, and garment subsystem described herein from those of known, or conventional, systems and techniques, including any prior designs invented by one or more inventors hereof. Certain unique features and combinations of features and structures supported and disclosed, herein, create a flexible therapeutic solution for prescription and administration by a wide variety of qualified human and veterinarian healthcare providers such as physicians, veterinarians, chiropractors, physical therapists, occupational therapists, athletic trainers, and the like.

Unlike conventional solutions, the design of the new spinal orthosis system disclosed herein aids in achieving control of gross movement of a mammalian patient trunk and control of intersegmental motion of the vertebrae in one or more planes of motion. The motion control afforded by the innovative custom-form spinal brace, which is uniquely custom-formed to anchor on the pelvis via lateral extensions from the spinal support panel (occasionally referred to herein as "pelvic wings"), and held in position with the aid of a unique anterior apron assembly having strapping, includes: lateral flexion (side bending) of the trunk in the coronal/frontal plane; anterior flexion (forward bending) of the trunk and posterior extension (backward bending) of the trunk in the sagittal plane; and axial rotation (twisting) of the trunk viewed in the transverse plane. The system is adapted to produce intracavitary pressure to reduce load on the intervertebral disks. More particularly, the spinal brace structure, along with garment subsystem and anterior apron assembly with strapping, facilitate training, or re-training, of the neuromotor system toward more-functional alignment.

BRIEF DESCRIPTION OF DRAWINGS

For purposes of illustrating the innovative nature, plus flexibility and genius of design and versatility of the new spinal bracing assembly/component and associated spinal brace system as applied to an underlying garment subsystem utilizing a feature-packed anterior apron assembly, figures are included (in which like numerals, where included, designate like parts). One can readily appreciate the advantages and novel features that distinguish the instant invention from conventional therapeutic spinal support systems and devices.

The figures as well as all incorporated technical materials have been included to communicate features of the innovation by way of example, only, and are in no way intended to unduly limit the disclosure hereof.

DESCRIPTION DETAILING FEATURES OF THE INVENTION

By viewing the figures and any technical reference materials incorporated by reference herein, one can further appreciate the unique nature of preferred and alternative features of the new spinal support brace structure 10, 100, 400, 410 and associated spinal orthosis system 200, 300, 500 disclosed herein. Back-and-forth reference and association has been made to various features and components represented by, or identified in, the figures. Structural and functional details have been incorporated herein, and shown schematically by way of example only, to showcase and highlight the genius and rigor behind the unique design of the unique orthoic system comprised of a novel thermoformable brace structure, anterior apron assembly with strapping, as releasably applied to the garment subsystem, as contemplated by this technical disclosure.

Figure 1:
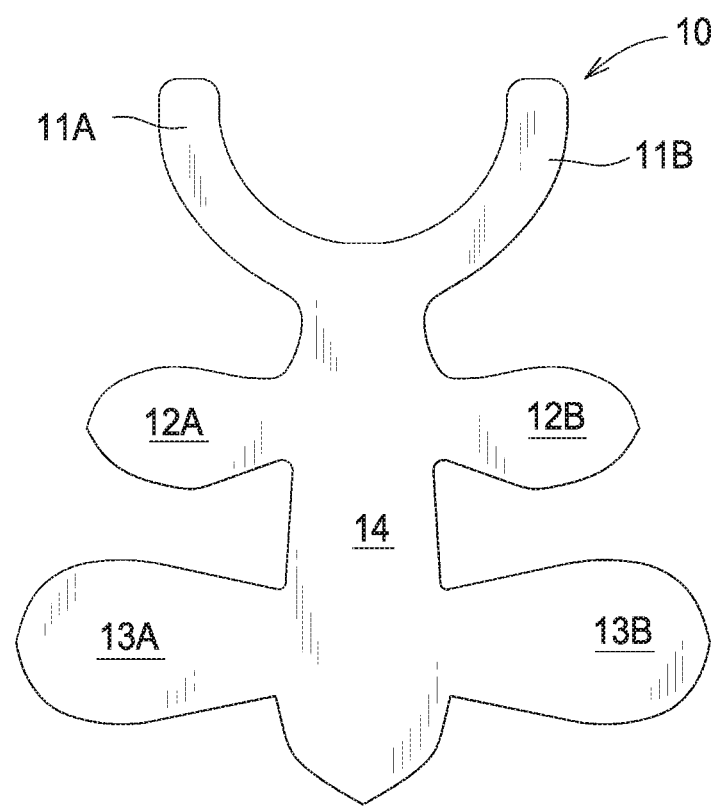
FIG. 1 is a top plan view schematically representing the outer circumference (planar, or flat in shape) of an alternative preferred spinal support brace component 10 of the invention having been cut to shape from, for example, a multi-layer laminated structure or a singular layer which is slid into a close-fitting sleeve of similar shape.

FIG. 1 schematically represents the outer circumference (a planar garment 'pattern') of an alternative preferred spinal support brace component 10 of the invention having been cut to shape from a thermoformable multi-layer laminated structure (for example, FIG. 7B), or alternatively, cut from a singular thermoformable layer which is slid into a close-fitting sleeve of the same shape (in a manner similar to sliding a thin pillow into a pillow case). While shown as a unitary design, a spinal support brace 10 may be composed of integrated features labeled as shown: a central support section ("spinal shaft") 14; first and second over-the-shoulder extensions ("shoulder straps") 11A, 11B; first and second rib extensions ("rib wings") 12A, 12B; and first and second lower extensions ("pelvic wings") at 13A, 13B. A qualified clinician (typically, an orthotist) receive the brace in this 'flattened' form and, unique to the instant invention, the clinician is able to custom-fit a brace 10 during or after examination once postural and/or anatomical structural indications have been identified for a patient, in accordance with physician, veterinarian, chiropractic, or other qualified prescription.

Figure 2:
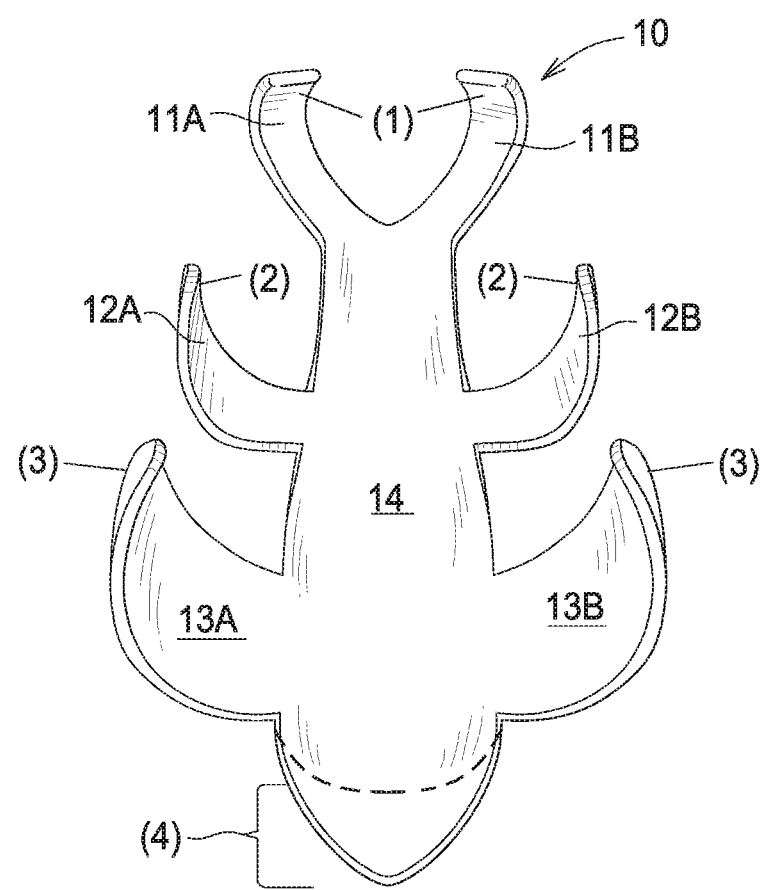
FIG. 2 is an isometric anterior aspect (front plan view) representing a spinal support brace component 10 after being molded/formed for customized fit out of a thermoformable material, to address structural or medical indications of a patient, as identified by a qualified clinician.
Figure 4:
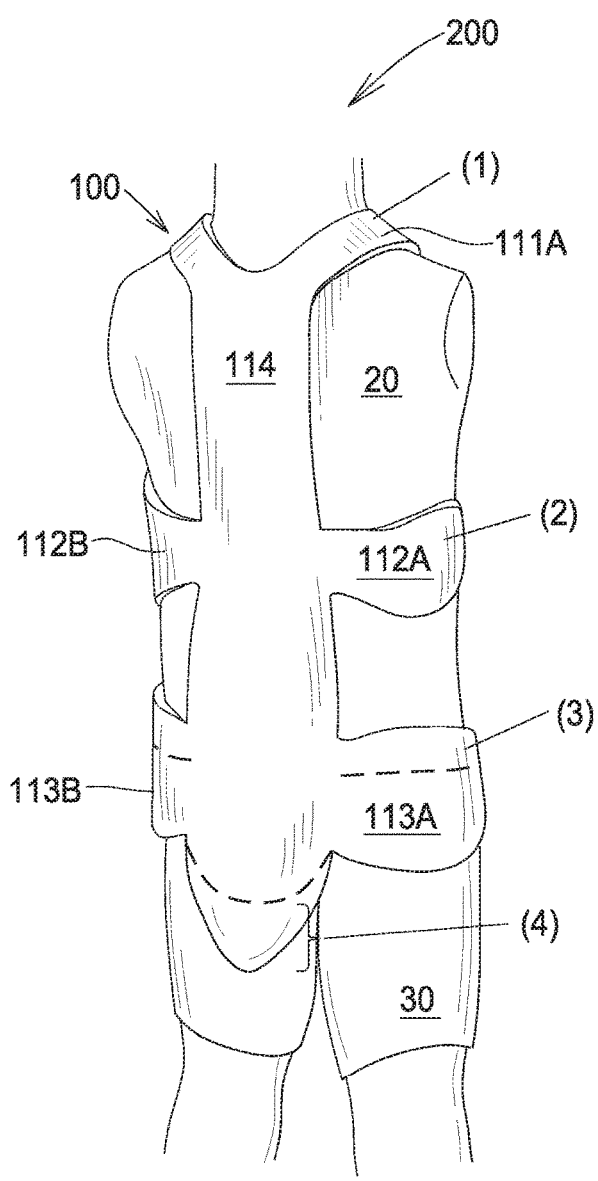
FIG. 4 is an isometric 3-D oblique posterior aspect (back view) depicting a preferred therapeutic spinal orthosis system 200 using alternative support bracing 100 sized for a young adult and applied by releasably securing the brace structure 100 to a garment subsystem that includes, for example, upper-torso component 20 and lower-torso component 30.
Figure 5:
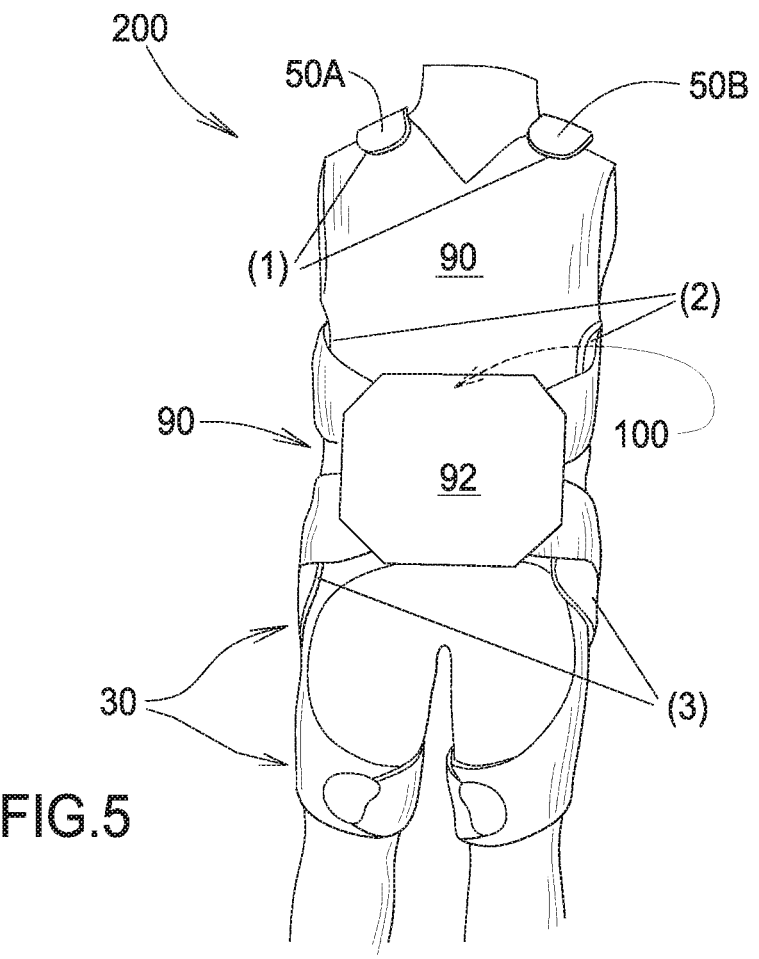
FIG. 5 is an isometric anterior aspect (front plan view) representing spinal orthosis system 200 of FIG. 4 comprising custom molded/formed spinal support brace 100 and an anterior apron assembly 90 having a panel 92 to which strapping pairs 92A-92B, 93A-93B are pivotally secured.
Figure 8:
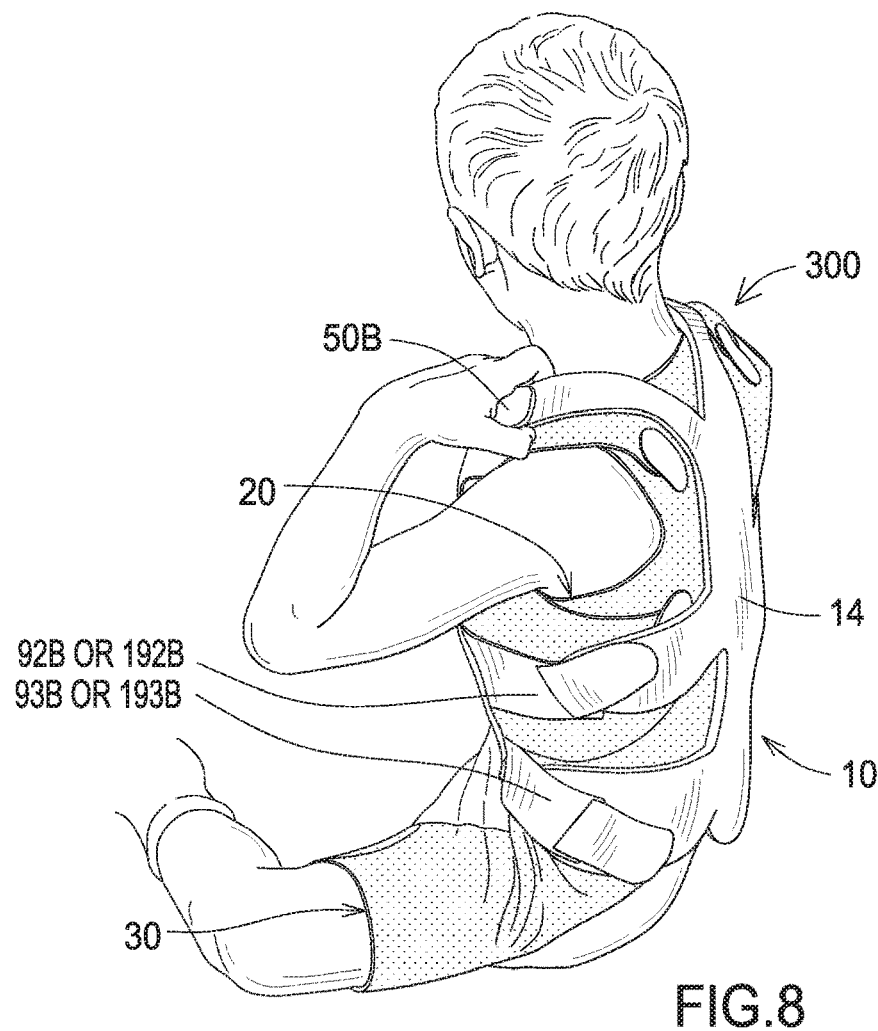
FIG. 8 is an isometric 3-D oblique posterior aspect (back view) depicting preferred alternative therapeutic garment subsystem 300 using support bracing structure 10 sized for a child and applied by releasably securing brace structure 10 to garment subsystem (20, 30).

The spinal support brace component 10 of FIG. 2 has been molded/formed for customized fit to address structural or medical indications of a patient, as identified by a qualified clinician. As one can appreciate from this 3-D rendering, an end-portion—pairs noted as (1), (2), (3)—has been labeled for each of the paired first and second extensions as shown: over-the-shoulder extensions (shoulder straps) 11A-11B; rib extensions (rib wings) 12A-12B; and lower extensions (pelvic wings) 13A-13B. FIG. 2 shows each end-portion formed inwardly (away from back plane toward the front) into a curvature for customized fit on a patient's back and around the trunk and pelvis, over the pelvic crests, providing an anchor for the spinal orthosis system 200 (FIGS. 4, 5). By way of example, spinal support brace 10 has been fit on a young human patient as shown in FIG. 8.

Figure 3:
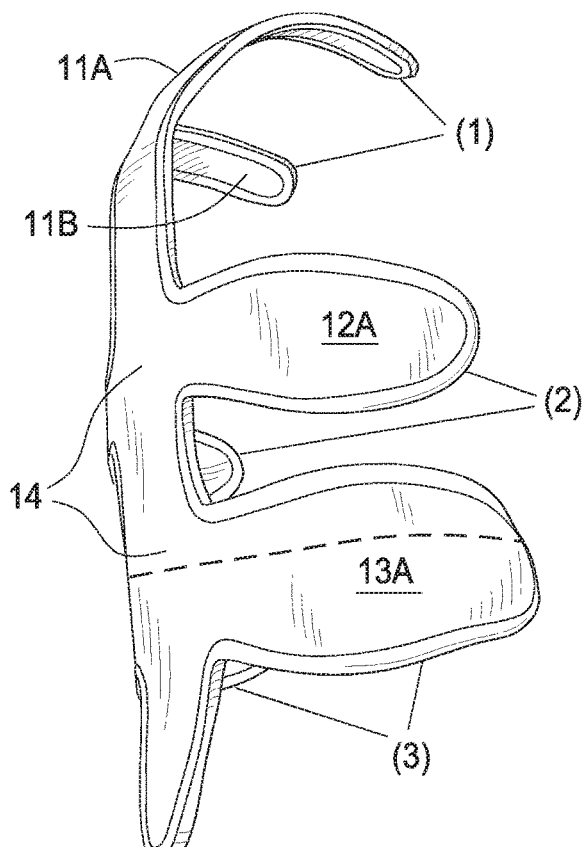
FIG. 3 is an isometric 3-D oblique rendering of the alternative preferred spinal support panel 10 of FIG. 2, once again, after it has been custom molded/formed for a particular patient.
Figure 7A:
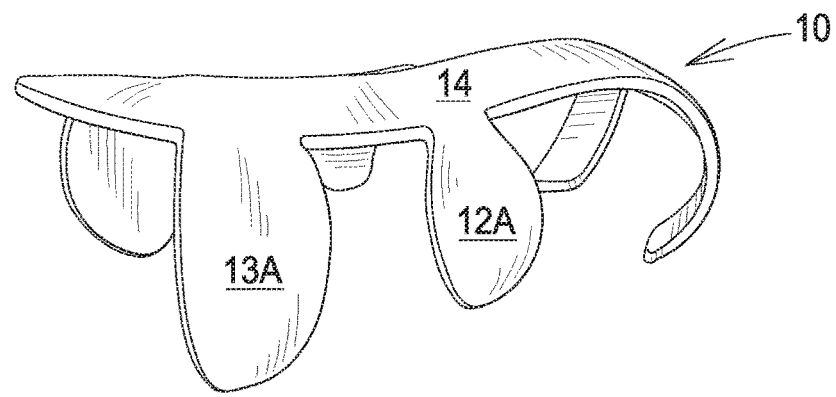
FIG. 7A is another isometric 3-D oblique rendering of spinal support brace 10, FIGS. 2 and 3, after being custom molded/formed for a particular patient.

FIG. 3 also depicts alternative preferred spinal support panel 10 of FIG. 2 after it has been custom molded/formed for a particular patient with an end-portion (1), (2), (3) of each extension respectively labeled 11A, B, 12A,B, and 13A,B having been formed into a curvature directed anteriorly (or, 'inwardly') away, from the back plane in which central support section (or, 'spinal shaft') 14 lies. FIG. 7A is another isometric 3-D oblique rendering of thermoformable spinal support brace 10 after being custom molded/formed for a particular patient.

The therapeutic spinal orthosis system 200, as shown in FIGS. 4, 5, includes alternative support bracing structure 100 sized for a young adult and applied by releasably securing brace structure 100 to an upper-torso component 20 and lower-torso component 30—collectively, herein referred to as a garment subsystem—structurally similar, for example, to those depicted in figures labeled PRIOR ART herein as ATTACHMENT A, selected from U.S. Pat. No. 8,007,457 (for example, FIGS. 18A,B 34, 38, 40, 41). Here, the brace structure 100 has been releasably applied to a therapeutic garment subsystem composed of an upper-torso component (such as that shown at 20) and lower-torso component (such as that shown at 30) as donned by a mannequin representing a human patient.

Figure 6:
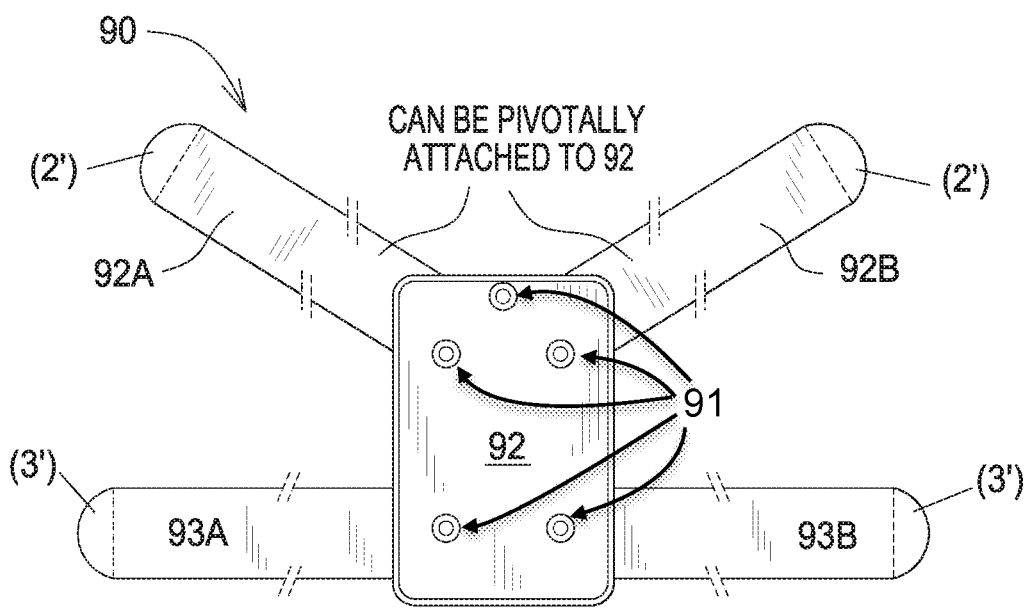
FIG. 6 is a top plan view schematically representing the outer circumference of features (planar in shape) of an alternative anterior apron assembly 90 including a central panel 92 for positioning over the midriff area (abdomen) of a patient such as is depicted in FIG. 5.

Spinal orthosis system 200 (FIG. 4) is depicted in FIG. 5 and shown with custom molded/formed spinal support brace 100 and an anterior apron assembly 90 having a panel 92 to which strap pairs 92A-92B, 93A-93B are secured. Turning to FIG. 6, at the free-end (labeled (2') and (3')) of each elongated strap of pairs 92A-92B, 93A-93B is an integrated releasable tab comprised of flexible mini-hooks similar to the structure of well-known VELCRO® hooks-and-loops (as detailed in U.S. Pat. No. 8,007,457) for releasable attachment to the outside of paired first and second extensions respectively labeled 112A-112B, and 113A-113B, see FIG. 4. As can be better seen in FIG. 4, first and second over-the-shoulder extensions 111A,B are releasably secured to upper-torso component 20 at respective extension end-portions (1). First and second rib extensions 112A,B are releasably secured by end-portions (2) by way of elasticized strapping 92A,B (FIG. 6). An end-portion (4) has been labeled for central support section (or, 'spinal shaft') 114: end-portion (4) can fall within a range depending upon whether the piece has been trimmed along dotted lines (often referred to as a 'trim line') as shown. First and second lower pelvic extensions 113A,B are releasably secured by respective end-portions (3) by way of elasticized strapping 93A,B (FIG. 6). Alternatively, elongated strap pairs 92A-92B, 93A-93B may be made of VELCRO® or similar hooks-and-loops strapping for attachment directly to the outer layer of garment subsystem (for example, upper- and lower-torso), leaving free-end tabs (2') and (3') available for application to address specific therapeutic benefit/effect. Preferred apron assembly 192 (referring to FIGS. 16-18) can be used to replace apron assembly 92 as described above in spinal orthosis system 200 of FIG. 4.

The alternative anterior apron assembly 90 of FIG. 6 includes a central panel 92 for positioning over the midriff area (abdomen) of a patient in a manner as depicted in FIG. 5. Each elongated strap of the pair 92A-92B is shown secured in pivot fashion to central panel 92 and each has a free-end labeled (2') with a tab of VELCRO®-type hooks for attachment to a respective end-portion (2) of rib extension 112A, 112B. Each elongated strap of pair 93A-93B is secured to central panel 92 and each has a free-end (3') with a tab of VELCRO®-type hooks for attachment to a respective end-portion (3) of pelvic extension 113A, 113B. See, also, FIGS. 16-18 depicting a preferred anterior apron assembly 190.

Figure 16:
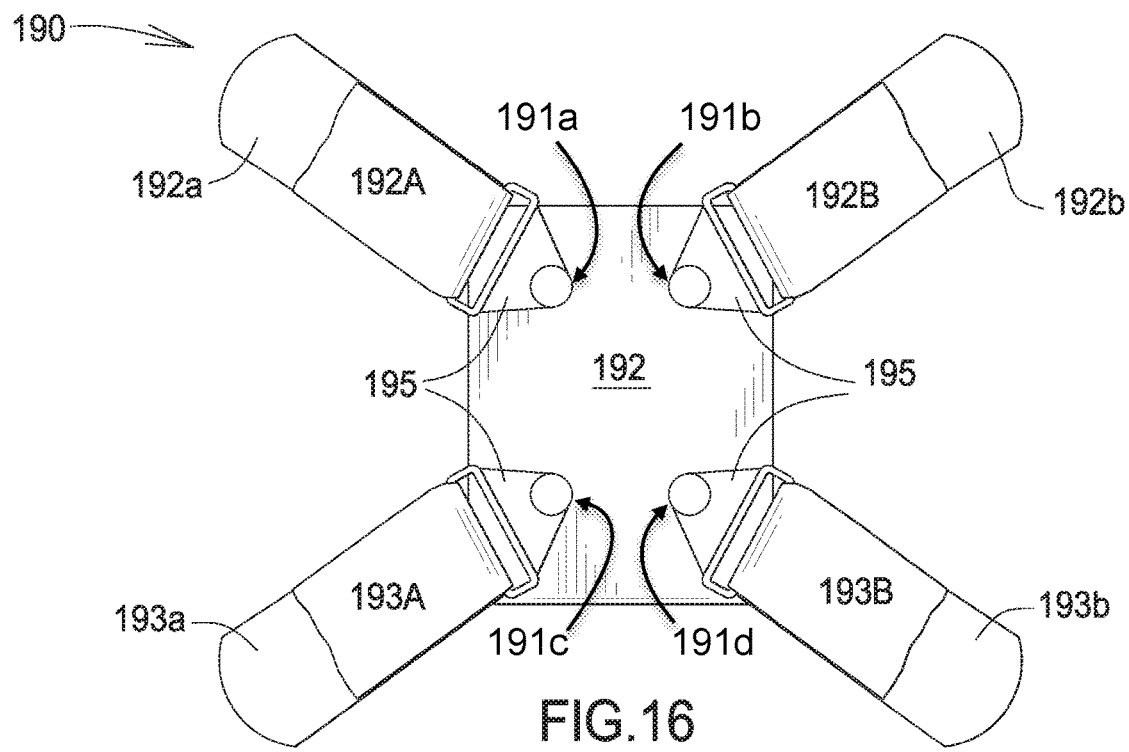
FIG. 16 is a top plan view schematically representing the outer circumference of features (planar) of a preferred anterior apron assembly 190 including a central panel 192 for positioning over the midriff area (abdomen) of a patient in a manner such as is depicted in FIGS. 5, 13, and 15.
Figure 17A:
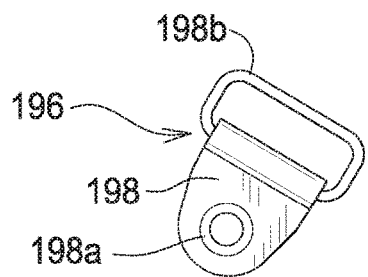
FIG. 17 is a top plan view schematically representing features of preferred chafe tabs 195, 196 in two different sizes to accommodate with of strapping 192A,B or 193A,B (see FIGS. 16 and 18) to which a chafe tab plate 197, 198 having a pivot aperture 197a, 198a is secured with a rectangular loop fastener 197b, 198b.
Figure 17B:
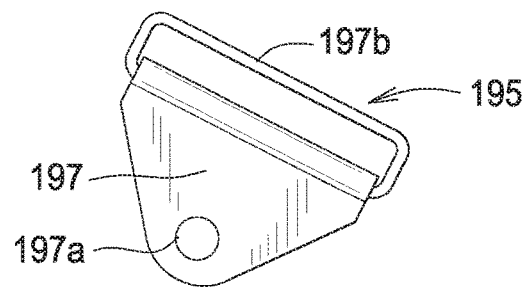
Figure 18:
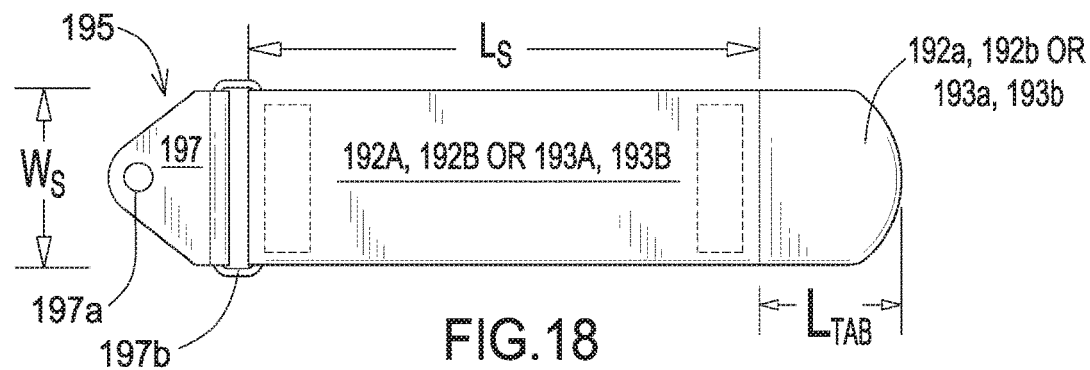
FIG. 18 is a top plan view schematically representing the outer circumference of features (planar) of preferred strapping of length $L_s$ (such as 192A,B or 193A,B) to which, by way of example, chafe tab 195 with chafe tab plate 197 is secured by way of rectangular loop 197b. Strapping end-portion 192a,b or 193a,b having length $L_{TAB}$, is shown secured to the other end of strapping 192A,B or 193A,B.

Jumping next, to FIGS. 16-18, this set of figures depict features of a preferred anterior apron assembly 190 shown with four straps, each pivotally and releasably secured with chafe tabs 195 or 198 to a corner of a rectangular central panel 192. The central panel is preferably a piece of compressed flexible foam. While shown adaptable for receiving the pivot point (197a, 198a) of each of four straps (for simplicity, labeled in pairs 192A,B and 193A,B) at a corner of panel 192, central panel 192 is preferably equipped with additional apertures so that additional pivot straps may be positioned as prescribed, to facilitate wearer comfort along with identified clinical objectives. As is the case for central panel 92 (FIGS. 5, 6), central panel 192 may vertically or horizontally span the abdomen pursuant to identified therapeutic objectives. Central panel 192 may accommodate total of four or more straps as shown in FIG. 16 at 192A,B, 193A,B, or more than four straps. And, if only four straps are used, additional apertures (five apertures shown at 91, FIG. 6; four apertures labeled 191a-d, FIG. 16) available on a central panel 192 provides a unique flexibility for clinicians to design and apply strapping configurations to accommodate a full range of therapeutic objectives. Further, use of additional apertures (five apertures shown at 91, FIG. 6; four apertures labeled 191a-d, FIG. 16) to receive rivets at pivot points 197a, 198a provide a clinician flexibility to modify—over a prescribed course of therapy—the location of straps on central panel 192.

Figure 7B:
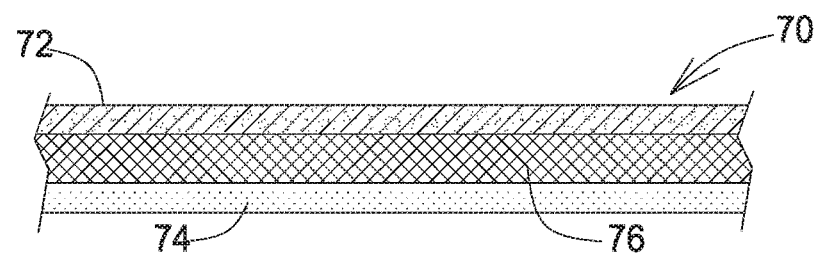
FIG. 7B is a sectional diagram highlighting one example of a suitable multi-layered (here, by way of example, three layers) laminate structure from which a brace 10, 100, 400, 410 shape can be cut.

FIG. 7B is a sectional diagram highlighting one example of a suitable multi-layered (here, by way of example, three layers) thermoformable laminate structure from which a brace 10, 100, 400, 410 shape can be cut or stamped using known techniques and equipment. A wide variety of alternative materials are suitable other than those specified. For example, while a 'polyester polyurethane foam' layer labeled 72 may be used, any suitable open-celled foam is contemplated. While a VELCRO®-type 'hook-sensitive' layer for accepting tabs of VELCRO®-type hooks (of, by way of example, nylon/lycra) is shown at 74, any suitable material having a stretch UBL (UnBroken Loop) character is contemplated. Interior layer 76 may be fabricated from a suitable low-temperature (moldable) thermoplastic, including a low-temp synthetic plastic polymer such as PVC, poly(vinyl chloride), or one selected from the polycaprolactones family of thermoplastics, that can be custom formed by a clinician to a patient is contemplated.

FIG. 8 is an isometric 3-D oblique posterior (back) view depicting a preferred alternative therapeutic garment subsystem 300 using support bracing component/structure 10 sized for a child and applied by releasably securing brace structure 10 to an upper-torso component 20 and lower-torso component 30—collectively, garment subsystem—which, by way of example, is shown structurally similar to those depicted in figures labeled PRIOR ART in ATTACHMENT A, selected from U.S. Pat. No. 8,007,457 (for example, FIGS. 18A,B, 34, 38, 40, 41).

Figure 9:
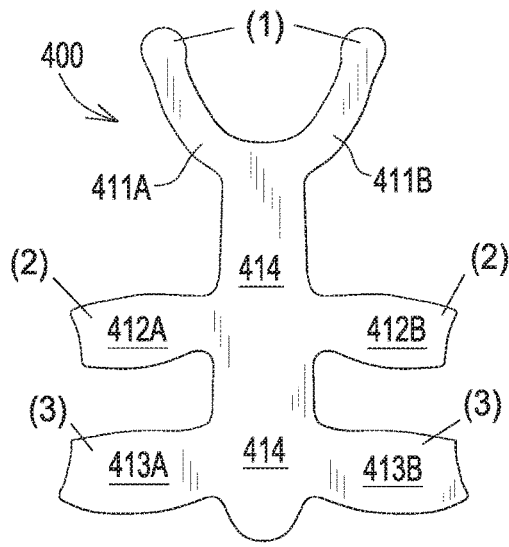
FIGS. 9,10 are top plan view schematically representing the outer circumference (planar, or flat in shape) of a preferred spinal support brace component 400 of the invention having been cut to shape.
Figure 10:
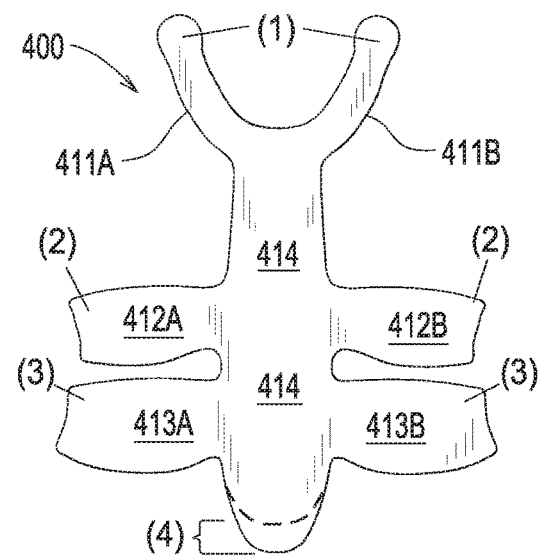
Figure 11:
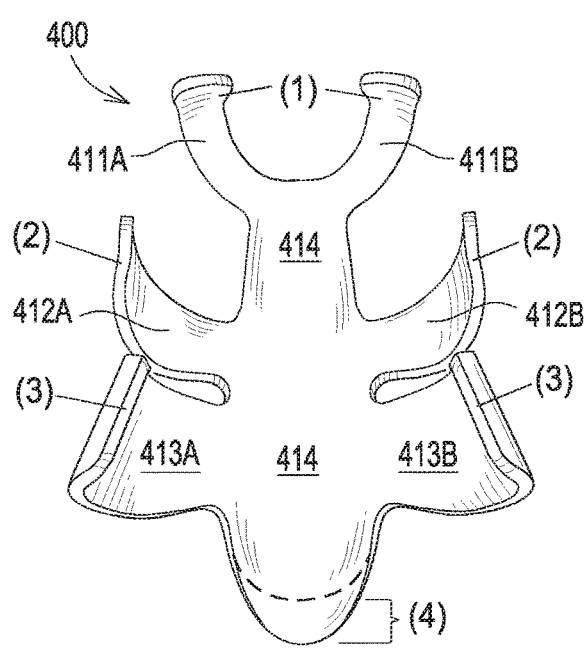
FIG. 11 is an isometric anterior aspect (front plan view) representing the preferred spinal support brace component 400 of FIGS. 9-10 after being molded/formed for customized fit to address structural or medical indications of a patient.

FIGS. 9-11 schematically depict, in a manner similar to FIG. 1 (a plan view of a garment pattern) and FIG. 2, (3-D rendering) of a preferred spinal support brace component 400 of the invention having been cut to shape from a multi-layer laminated structure (for example, FIG. 7B), or alternatively, cut from a singular layer which is slid into a close-fitting sleeve of the same shape (in a manner similar to sliding a thin pillow into a pillow case). While shown as a unitary design, a spinal support brace 400 may be composed of integrated features labeled as shown: a central support section ("spinal shaft") 414; first and second over-the-shoulder extensions ("shoulder straps") 411A, 411B; first and second rib extensions ("rib wings") 412A, 412B; and first and second lower extensions ("pelvic wings") at 413A, 413B. Each of the extensions has an end-portion (1), (2), (3), as does central support section 414 at (4). End-portion (4) may fall within a range, as shown in FIGS. 10-11 and formed by cutting along dotted lines known as a 'trim line'. A qualified clinician (typically, an orthotist) receive the brace in this 'flattened' form and, unique to the instant invention, the clinician is able to custom-fit a brace 400 during or after examination once postural and/or anatomical structural indications have been identified for a patient, in accordance with physician, veterinarian, chiropractic, or other qualified prescription.

Figure 12:
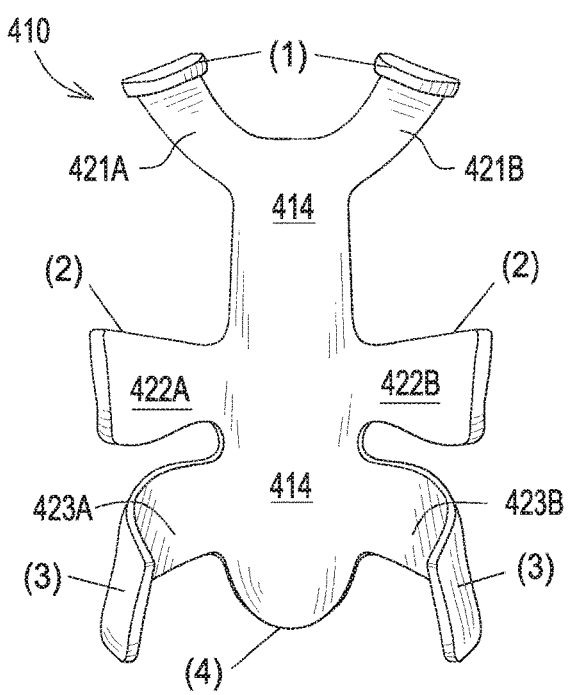
FIG. 12 is an isometric anterior aspect (front plan view) representing an alternative preferred spinal support brace component 410 after being molded/formed for customized fit to address structural or medical indications of a patient

FIGS. 11-12 are isometric anterior aspects (front plan views) representing alternative molded shapes of spinal support braces, respectively labeled 400 and 410, after being molded/formed for customized fit to address structural or medical indications of a patient, as identified by a qualified clinician. As one can appreciate, end-portion pairs (1), (2), and (3) of associated extension pairs ("wings") have been curved anteriorly (or, 'inwardly') from back central support sections (spinal shaft) 414 toward the front, in a manner similar to that depicted in FIGS. 2, 3, 4, 7A.

Figure 13:
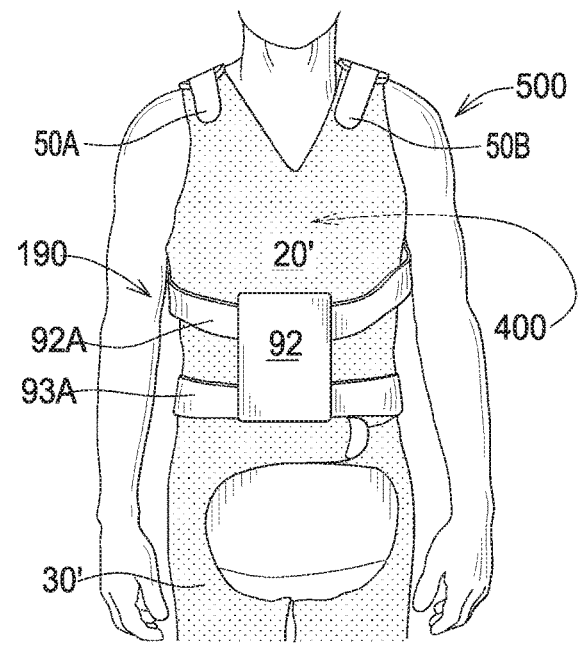
FIG. 13 FIG. 14 FIG. 15 are, respectively, isometric 3-D oblique anterior aspect (front plan view), posterior aspect (back view), and lateral aspect (side view) depicting a preferred therapeutic spinal orthosis system 500 using alternative support bracing 400 sized for an adult and applied by releasably securing the brace structure 400 to a garment subsystem that includes, for example, upper-torso component 20' and lower-torso component 30'.
Figure 14:
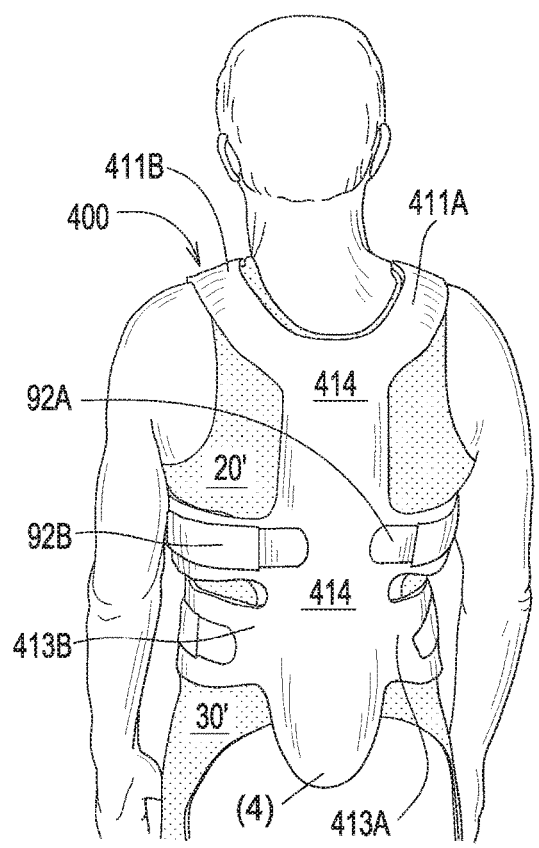
Figure 15:
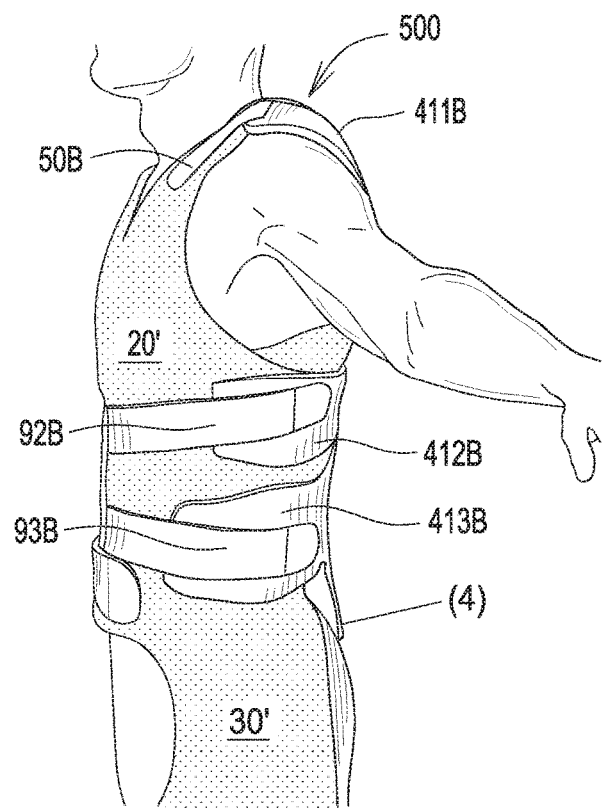

Turning to FIGS. 13-15, preferred spinal orthosis system 500 is depicted on an adult patient with custom molded/formed spinal support brace 400 (shown, also, in FIGS. 9-11) and alternative preferred apron assembly 90 (FIGS. 5-6). Apron assembly 90 can be replaced with preferred anterior apron assembly 190 (detailed in FIGS. 16-18). Apron assembly 190 has a central panel 192 to which strap pairs 192A,B, and 193A,B of preselected length $L_s$ (FIG. 18) for therapeutic application to mid- and lower extensions 412A,B and 413A,B, are releasably secured with chafe tabs 195 of suitable width $W_s$ (FIG. 18) to accommodate the width of the tab 195.

A support brace of the invention such as shown at 10, 100, 400, 410 is adapted for use with a unique anterior apron assembly 90, 190 consisting of a piece of flexible material 92, 192 attached to elasticized strapping 92A, 92B, 93A, 93B (and in the case of assembly 190 strapping 192A, 192B, 193A, 193B) designed to vertically or horizontally span the abdomen (midriff area). The apron assembly 90, 190 attaches to the spinal support brace 10, 100, 400, 410 to hold it comfortably in place on the wearer's body to achieve therapeutic objectives. The spinal support brace 10, 100, 400, 410 is preferably made of low-temperature thermoplastic, lined with non-slip foam or other soft absorbent material on the inside (against the underlying garment subsystem), and lined with hook-compatible "unbroken loop (UBL)" fabric on the outside. When donning and wearing the spinal support brace 10, 100, the straps of the anterior apron panel are releasably affixed, under tension, to the exterior surface of the spinal support brace by means of hook material "tabs", and the over-the-shoulder extensions of the spinal support brace are attached to the upper-torso component of the underlying garment subsystem by means of hook material tabs. The two components of the spinal support system are thus connected together and to the underlying garment subsystem in any of an infinite number of arrangements designed to create a comfortable spinal support environment customized to that wearer and customized to support therapeutic or treatment objectives.

The spinal support shaft 14, 414 need not be curved to fit the wearer's (patient) spine. The spinal panel/brace 10, 100, 400, 410 is adapted for customization by an orthotist to address identified therapeutic objectives of a patient. The panel/brace can be re-warmed and adjusted to address changes to the patient's posture, spinal alignment, or to otherwise reflect progress towards therapeutic objectives. By way of example, only, a clinician may, during customization of a spinal brace/panel 10, 100, 400, 410 maintain a straight shape for spinal support shaft 14, 414 so as not to reinforce a wearer's existing kyphosis (swayback). Alternatively, it may be determined upon analysis and further study that leaving the spinal shaft 14, 414 effectively straight will provide enough gentle encouragement of the wearer's spine to gradually straighten over time.

In a customizing process typically referred to as "warm-and-form" molding, the thermoformable spinal support brace is heated to an appropriate temperature by the clinician, according to a prescribed procedure, and then shaped in place onto the individual wearer's body, where it cools and hardens into a rigid brace customized to that wearer's body.

As shown throughout, spinal support brace 10, 100, 400, 410 is uniquely designed with a single spinal support shaft and six extensions: two upper extensions ("shoulder arm" pairs labeled 11A,B, 111A,B, 411A,B, 421A,B) molded/formed to fit over the shoulders of the wearer; two "rib wings" (pairs labeled 12A,B, 112A,B, 412A,B, 421A,B) molded/formed to fit around the ribcage of the wearer to maximize the stability of the spinal support brace during the wearer's movement, and to provide lateral support for the torso; and two "pelvic wings" (pairs labeled 13A,B, 113A,B, 413A,B, 423A,B) molded/formed to fit around and over the wearer's pelvis and illiac crest to maximize the stability of the spinal support brace during the wearer's movement, and to provide an anchoring point for the spinal support brace to support therapeutic or treatment objectives. The thermoformable spinal support shaft 14, 114, 414 is preferably molded to the wearer's spine (as determined by a qualified clinician or provider) via a warm-and-form (the application of heat and pressure) process according to therapeutic objectives. Such objectives include, but are not limited to: a) support the spine in it's current postural position and prevent movement; b) 'splint' the spine with a corrected support to encourage it to adapt to the corrected position; and others.

Due to the unique low-temperature thermoplastic composition of the device, the spinal support shaft and each or all of the six extensions (brace 10 pairs labeled 11A-11B, 12A-12B, 13A-13B and brace 100 pairs labeled 111A-111B, 112A-112B, 113A, 113B, brace 400 pairs labeled 411A-411B, 412A-412B, 413A-413B, and brace 410 pairs labeled 421A-421B, 422A-422B, 423A-423B) can be softened by heat and re-molded by a skilled clinician multiple times to maintain the device's fit for maximum therapeutic value and wearer comfort; to address changes in the wearer's torso; and/or to address changes to the therapeutic or treatment objectives it supports. The thermoformable feature of the spinal brace device permits a clinician to mold the brace to provide either structural support or corrective forces to the wearer's existing musculoskeletal system.

An underlying garment subsystem can be made of an upper-torso garment ("TankTop" such as is shown at 20 in FIGS. 4, 5, 8 and 20' in FIGS. 13-15, see ATTACHMENT A by way of example) and a lower-torso garment ("Hipster" such as is shown at 30 in FIGS. 4, 5, 8 and 30' in FIGS. 13-15, see ATTACHMENT A by way of example), each of which may be a unitary piece or composed of a plurality of pieces outlining a unique shape cut from a multi-layer elasticized material selected for: its ability to grip the skin and soft tissues of the wearer; its ability to accept attachment of external non-slip elasticized strapping; and its ability to allow air flow and moisture evaporation to reduce heat retention and allow for the wearer's skin temperature regulation. An underlying garment subsystem may also be composed of a front and back piece donned by a patient/wearer in jumpsuit fashion interconnected at the shoulders and strapping applied laterally along the sides, for example. Alternatively, the garment subsystem may be composed of upper- and lower-torso pieces of a wide variety of outer perimeter shapes. See, by way of example, ATTACHMENTS B and C, incorporated herein by reference, depict underlying garment subsystem products designed by at least one co-inventor hereof and offered by the applicant-assignee of the instant invention.

Once fit to the wearer (whether a human infant, toddler, child, adult, or other mammal), removable elongated elasticized strapping pieces are positioned onto the available outer field according to identified therapy or treatment objectives. The strapping acts as external muscle to position the body part in optimal functional alignment; to resist movement where indicated by therapeutic objectives; and to enable or enhance movement where indicated by therapeutic objectives.

The instant invention allows for maximum availability of a stable field area (supported by a comfortable non-slip undersurface) and, therefore, great flexibility in positioning of the elasticized pieces that can therapeutically aid the wearer.

The exterior surface of the spinal support brace presents a stretch fabric, such as a nylon/Lycra™ blend, finished with an unbroken loop (UBL) exterior that will accept removable 'hook' fasteners (similar to VELCRO® hook-and-loop materials).

The interior surface of the spinal support brace presents a compressible open-celled foam material, such as a polyester/polyurethane foam, that provides a cushioning, evaporation, and airflow layer between the brace material and the wearer's body.

These interior and exterior materials may be affixed to the thermoplastic layer via a number of methods, including but not limited to:

a) A heat-and-pressure lamination process in which the interior and exterior layers are laminated to the thermoplastic layer using an adhesive film, spray, liquid or powder;

b) A 'fitted sleeve" method in which the exterior UBL material and the interior foam material are independently sewn, welded, or otherwise bonded together into a single- or multi-piece cover that is manually fitted over the thermoplastic layer of the spinal support brace and closed snugly with releasable fittings. The fitted sleeve method also allows the cover to be removed for laundering.

The exterior UBL surface of the spinal support brace allows for the infinitely adjustable releasable attachment of the spinal support brace to the underlying garment subsystem, or to the anterior panel, as follows:

a) The over-the-shoulder extensions of the customized spinal support brace (FIG. 2-3 at 11A,B, FIG. 4 at 111A,B, FIGS. 9-11 at 411A,B, FIGS. 14-15 at 411A,B, and FIG. 12 at 421A,B) are releasably attached to the underlying garment system in the wearer's clavicle area (FIGS. 5 and 16 at 50A,B) using hook material. The attachment points are selected to ensure a snug fit of the spinal support brace, and to support the clinician's therapeutic and/or rehabilitation objectives.

b) The rib extensions of the customized spinal support brace (FIGS. 2-3 at 12A,B, FIG. 4 at 112A,B, FIGS. 9-11 at 412A,B, FIGS. 14-15 at 412A,B, and FIG. 12 at 422A,B) are releasably attached to the upper elasticized strapping of the anterior panel with the same hook material (FIG. 6 at 92A,B, and FIG. 16 at 192A,B). The strap attachment points are selected to ensure a snug fit of the spinal support brace, and to support the clinician's therapeutic and/or rehabilitation objectives. Uniquely, the rib extensions also enclose the patient's thoracic cage to provide truncal stability, prevent motion in the sagittal plane, and support intracavitary pressure—without excessive compression.

c) The pelvic extensions of the customized spinal support brace (FIGS. 2, 3 and 7A at 13A,B, FIG. 4 at 113A,B, FIGS. 9-11 at 413A,B, FIGS. 14-15 at 413A,B, and FIG. 12 at 423A,B) are releasably attached to the lower elasticized strapping of the anterior panel with the same hook material (FIG. 6 at 93A,B, and FIG. 16 at 193A,B). The strap attachments points are selected to ensure a snug fit of the spinal support brace, and to support the clinician's therapeutic and/or rehabilitation objectives. Uniquely, the pelvic extensions are formed during customization to overlap and rest atop the patient's pelvic crest, anchoring the bottom of the spinal panel to the pelvis, and creating a solid one-piece support structure that attaches the patient's shoulders to his/her pelvis for maximum stability—without excessive compression.

EXAMPLES of the unique preferred and alternative structures and features are shown and described throughout. And, while certain representative embodiments and details have been shown for the purpose of illustrating features of the invention, those skilled in the art will readily appreciate that various modifications, whether specifically or expressly identified herein, may be made to these representative embodiments without departing from the novel core teachings or scope of this technical disclosure. Accordingly, all such modifications are intended to be included within the scope of the claims. Although the commonly employed preamble phrase "comprising the steps of" may be used herein, or hereafter, in a method claim, the applicants do not intend to invoke any statutory section in a manner that unduly limits rights to the claimed invention. Furthermore, in any claim that is filed herewith or hereafter, any means-plus-function clauses used are intended to cover at least all structure(s) described herein as performing the recited function and not only structural equivalents but also equivalent structures.

We claim:

1. A thermoformable spinal brace for customizable warm-and-form shaping to a wearer adapted for donning on the wearer along with an anterior apron assembly, comprising:
   (a) the thermoformable spinal brace comprising first and second integral over-the-shoulder extensions, first and second integral rib extensions, and first and second integral lower extensions, wherein each said first and second integral lower extension comprises an end-portion curved anteriorly away from a back spinal support section of the spinal brace adapted to overlap at least a portion of a pelvis area of the wearer upon donning;
   (b) the anterior apron assembly comprising a central panel from which a secured end of each of a plurality of straps pivotally extends;
   (c) a free-end of each of a first and second straps of said plurality of straps extending from said anterior apron is adapted for releasable attachment to said end-portion of a respective one of said first and second integral lower extensions; and (d) a free-end of each of a third and fourth straps of said plurality of straps extending from said anterior apron is adapted for releasable attachment to said end-portion of a respective one of said first and second intergral lower extensions.

2. The thermoformable spinal brace and anterior apron assembly of claim 1 wherein:
the thermoformable spinal brace is fabricated of at least a thermoplastic material; and
said central panel of the anterior apron assembly is made of a compressed flexible foam having a plurality of apertures, each of said apertures adapted to assist in securing said secured end of at least one of said plurality of straps pivotally extending from said central panel.

3. The thermoformable spinal brace and anterior apron assembly of claim 1 wherein, upon donning the thermoformable spinal brace and the anterior apron assembly, said free-end of said first strap of said plurality of straps is releasably attached to said end-portion of said first integral lower extension, said free-end of said second strap of said plurality of straps is releasably attached to said end-portion of said second integral lower extension, said free-end of said third strap of said plurality of straps is releasably attached to said end-portion of said first rib extension, and said free-end of said fourth strap of said plurality of straps is releasably attached to said end-portion of said second rib extension.

4. The thermoformable spinal brace of claim 1 wherein said customizable warm-and-form shaping hardened said first and second integral over-the-shoulder lower extensions and hardened said first and second integral lower extension for said donning on the wearer.

5. The thermoformable spinal brace of claim 1 wherein, upon donning the thermoformable spinal brace and the anterior apron assembly:
said free-end of each of said first and second straps extending from said anterior apron assembly is releasably attached to said end-portion of said respective one of said first and second integral lower extensions having been hardened by said warm-and-form shaping.

6. The thermoformable spinal brace of claim 5 further comprising:
(a) each of said first and second intergal over-the-shoulder extensions has an end-portion adapted to overlap at least a portion of a respective shoulder of the wearer upon donning; and
(b) the thermoformable spinal brace is adapted for donning on the wearer over an underlying garment subsystem covering a portion of the wearer's upper-torso.

7. The thermoformable spinal brace of claim 6 wherein each said end-portion of said first and second integral over-the-shoulder extension is releasably attached to said underlying garment subsystem overlapping said portion of said respective shoulder in a clavicle area of the wearer.

8. The thermoformable spinal brace of claim 1 further adapted for donning on the wearer over an underlying garment subsystem covering at least a portion of the wearer's upper-torso, the spinal brace further comprising:
each said first and second integral over-the-shoulder extensions has an end-portion adapted to overlap at least a portion of a respective shoulder of the wearer upon donning, each said end-portion of said first and second shoulder extension adapted for releasable attachment to an area of said portion of the wearer's upper-torso of said underlying garment subsystem.

9. A spinal orthosis system comprising a thermoformable spinal brace for customizable warm-and-form shaping to a wearer adapted for donning on the wearer along with an anterior apron assembly, the thermoformable spinal brace comprising first and second integral over-the-shoulder extensions each having an end-portion adapted to overlap at least a portion of a shoulder of the wearer upon donning, first and second integral rib extensions, and first and second integral lower extensions each having an end-portion adapted to curve anteriorly away from a back spinal support section of the spinal brace and adapted to overlap at least a portion of a pelvis area of the wearer upon donning, wherein:
(a) said first and second integral rib extensions each have an end-portion adapted to overlap at least a portion of a ribcage of the wearer upon donning; and
(b) the thermoformable spinal brace further comprises:
(i) a free-end of each of a first and second straps extending from said anterior apron assembly is adapted for releasable attachment to said end-portion of a respective one of said first and second integral lower extensions; and
(ii) a free-end of a third strap extending from said anterior apron is adapted for releasable attachment to an end-portion of said first rib extension, and a free-end of a fourth strap extending from said anterior apron assembly is adapted for releasable attachment to an end-portion of said second integral rib extension.

10. The spinal orthosis system of claim 9 wherein, upon donning the thermoformable spinal brace and the anterior apron assembly:
(a) a free-end of a first and second strap extending from said anterior apron assembly is releasably attached to said end-portion of said respective one of said first and second integral lower extensions; and
(b) a free-end of a third strap extending from said anterior apron is releasably attached to said end-portion of said first integral rib extension, and a free-end of a fourth strap extending from said anterior apron assembly is releasably attached to said end-portion of said integral second rib extension.

11. The spinal orthosis system of claim 9 wherein said warm-and-form shaping hardened said first and second integral over-the-shoulder extensions, and further adapted for donning on the wearer over an underlying garment subsystem covering at least a portion of the wearer's upper-torso, and wherein each said end-portion of said first and second integral over-the-shoulder extension is releasably attached using at least one tab to said area of said underlying garment subsystem overlapping said at least a portion of a shoulder.

12. The spinal orthosis system of claim 9 wherein said customizable warm-and-form shaping hardened each said end-portion of said first and second integral lower extension and said first and second integral rib extension to accept attachment of said respective free-end of one of a plurality of straps, and hardened said first and second integral over-the-shoulder extensions.

13. A spinal orthosis system comprising a thermoformable thermoplastic spinal brace for customizable warm-and-form shaping to a wearer adapted for donning on the wearer over an underlying garment subsystem covering a portion of the wearer's upper-torso and a portion of the wearer's lower-torso; the thermoformable spinal brace comprising first and second integral over-the-shoulder extensions each having an end-portion adapted to overlap at least a portion of a shoulder of the wearer upon donning, first and second rib extensions, and first and second lower extensions each having an end-portion curved inwardly away from a back spinal support section of the spinal brace; wherein upon donning, each said end-portion of said first and second integral over-the-shoulder extension is adapted for releasable attachment to an area of said portion of the wearer's upper-torso of said underlying garment subsystem; the spinal orthosis system further comprising:

(a) an anterior apron assembly comprising a central panel from which a secured end of each of a plurality of straps extends;
(b) a free-end of each of first and second straps of said plurality of straps extending from said anterior apron assembly is releasably attached to said end-portion of a respective one of said first and second lower extensions; and
(c) a free-end of each of third and fourth straps of said plurality of straps extending from said anterior apron assembly is releasably attached to said end-portion of a respective one of said first and second rib extensions.

14. The spinal orthosis system of claim 13 wherein said customizable warm-and-form shaping hardened said first and second integral over-the-shoulder extensions and hardened said first and second lower extensions for said donning on the wearer.

15. The spinal orthosis system of claim 13 donned on the wearer and wherein:

said warm-and-form shaping hardened each said end-portion of said first and second integral over-the-shoulder lower extensions, each said end-portion of said first and second integral over-the-shoulder lower extensions releasably attached using at least one tab to said area of said underlying garment subsystem overlapping said portion of said shoulder.

* * * * *